United States Patent
Wang et al.

(10) Patent No.: US 8,399,718 B2
(45) Date of Patent: Mar. 19, 2013

(54) PROMOTED COPPER/ZINC CATALYST FOR HYDROGENATING ALDEHYDES TO ALCOHOLS

(75) Inventors: Justin X. Wang, Louisville, KY (US); Jason E. Spencer, Palmyra, IN (US); Yeping Cai, Louisville, KY (US)

(73) Assignee: Sud-Chemie Inc., Louisville, KY (US)

( * ) Notice: Subject to any disclaimer, the term of this patent is extended or adjusted under 35 U.S.C. 154(b) by 205 days.

(21) Appl. No.: 12/960,808

(22) Filed: Dec. 6, 2010

(65) Prior Publication Data

US 2012/0142978 A1 Jun. 7, 2012

(51) Int. Cl.
- *C07C 29/14* (2006.01)
- *B01J 37/08* (2006.01)
- *B01J 23/89* (2006.01)
- *B01J 23/80* (2006.01)

(52) U.S. Cl. ......... 568/881; 568/885; 502/329; 502/343

(58) Field of Classification Search .................. 568/881, 568/885; 502/329, 343
See application file for complete search history.

(56) References Cited

U.S. PATENT DOCUMENTS

| | | | |
|---|---|---|---|
| 4,393,251 A | 7/1983 | Broecker et al. | |
| 4,562,174 A | 12/1985 | Stiles | |
| 4,762,817 A | 8/1988 | Logsdon et al. | |
| 4,876,402 A | 10/1989 | Logsdon et al. | |
| 5,302,569 A | 4/1994 | Horn et al. | |
| 5,334,779 A | 8/1994 | Kuo | |
| 5,395,989 A | 3/1995 | Yoneoka et al. | |
| 5,714,644 A | 2/1998 | Irgang et al. | |
| 6,350,923 B1 | 2/2002 | Eller et al. | |
| 6,600,078 B1 | 7/2003 | Mahmud et al. | |
| 6,693,057 B1 | 2/2004 | Cai et al. | |
| 7,064,097 B1 | 6/2006 | Cai et al. | |
| 7,084,312 B1 | 8/2006 | Huber et al. | |

FOREIGN PATENT DOCUMENTS

CN 1695802 11/2005

OTHER PUBLICATIONS

International Search Report and the Written Opinion of the International Searching Authority, or the Declaration [Form PCT/ISA/220] with Feb. 14, 2012 Date of Mailing.

*Primary Examiner* — Sikarl Witherspoon
(74) *Attorney, Agent, or Firm* — Scott R. Cox

(57) ABSTRACT

A catalyst for hydrogenating aldehydes to alcohols includes a combination of copper oxide and zinc oxide and promoters including one or more alkaline earth metal promoters and/or one or more transition metal promoters. The promoters may be combined with copper oxide and zinc oxide after formation of a copper/zinc precursor material.

15 Claims, No Drawings

PROMOTED COPPER/ZINC CATALYST FOR HYDROGENATING ALDEHYDES TO ALCOHOLS

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in light of this purpose, and not as admissions of prior art.

One embodiment of the present invention relates to catalytic hydrogenation of aldehydes to alcohols. Another embodiment of the invention discloses improved catalysts for the catalytic hydrogenation of aldehydes to the corresponding alcohols. A further embodiment discloses processes for the production of the improved catalysts for the hydrogenation of aldehydes to the corresponding alcohols. A further embodiment discloses catalytic processes for hydrogenating aldehydes to the corresponding alcohols utilizing the improved catalyst.

Aldehydes and alcohols are two general classes of organic compounds. Hydrogenation of aldehydes to produce the corresponding alcohols is a major class of organic chemical processes. These processes have long been practiced. In the conventional process the reaction of an aldehyde with hydrogen generally is carried out in the presence of certain reduced metal compounds, which act as hydrogenation catalysts. The conventionally used catalysts for this reaction include copper catalysts, such as copper chromite or copper/zinc oxides; nickel catalysts, such as nickel and nickel compounds with promoters; and cobalt catalysts, such as cobalt compounds with promoters.

The hydrogenation catalysts that have previously been disclosed often exhibit one or more disadvantages when used for commercially hydrogenating aldehydes to alcohols. For example, some of the prior art catalysts are difficult to prepare and have serious toxicity problems associated with their use (e.g. chromium.) Some of catalysts are significantly costly (e.g. cobalt). Some of the catalysts exhibit less than desired selectivity (e.g. nickel and copper) or produce significant amounts of by-products, such as ethers or esters. Such by-products generally must be removed from the hydrogenation product stream prior to subsequent use.

When using nickel catalysts for this process, the principal by-products produced are ethers and hydrocarbons, particularly paraffins. For example, in the catalytic hydrogenation of butyl aldehyde to butanol over a nickel catalyst, butyl ether is produced. The ethers form azeotropes with the alcohol hydrogenation products and water that frequently is present in the product from the feed stream. A substantial effort is necessary to separate these by-products from the alcohols and a significant loss of alcohol is normally encountered.

When copper oxide/zinc oxide catalysts are used for this process, esters are the principal by-product. For example, in the catalytic hydrogenation of butyl aldehyde to butanol over a copper oxide/zinc catalyst, butyl butyrate is produced.

To compensate for the gradual loss of catalytic activity of these hydrogenation catalysts over time, it is conventional practice to increase the reaction temperature. When using reduced copper oxide/zinc oxide catalyst, however, such temperature increases lead to increased formation of the undesired ester by-products, thus further complicating subsequent product purification procedures or necessitating an early change in the catalyst charge.

One widely used catalyst for this reaction is a copper oxide/zinc oxide catalyst as disclosed by U.S. Pat. Nos. 4,876,402 and 4,762,817. These patents disclose the use of alkali metal selectivity enhancers and transition metal selectivity enhancers in combination with the copper oxide and zinc oxide. However, with the technology disclosed therein, either undesired ethers and paraffins tend to be produced or catalytic performance and mechanical strength of the final catalysts are degraded. Further, the leaching rate of the alkali enhancers is high, which often results in a degradation of selectivity over time on stream.

CN 1695802 also discloses catalysts for preparing alcohols from aldehydes in gas phase, which catalysts are produced by a specific two step precipitation process. Catalysts made by this process have reduced selectivity and activity over other prior art catalysts.

Accordingly, a need exists to produce catalysts for the catalytic hydrogenation of aldehydes to corresponding alcohols with improved product selectivity and reduced by-product production while catalytic activity and mechanical strength remain high. Further, improved processes for the production of catalysts that are useful for catalytic hydrogenation of aldehydes to corresponding alcohols and which exhibit improved selectivity and activity are also important.

SUMMARY OF THE INVENTION

One embodiment of the present invention provides a catalyst for hydrogenating aldehydes to corresponding alcohols comprising from about 10 to about 70% by weight copper oxide, from about 30 to about 90% by weight zinc oxide, and further comprising specific promoters, wherein the promoters consist of one or more alkaline earth metals and/or one or more transition metals.

The invention also comprises a process for the production of a catalyst for hydrogenating aldehydes to corresponding alcohols. The precursor catalyst containing copper oxide and zinc oxide can be made by blending of a zinc compound and a copper compound and fusing the mixture followed by grinding, decomposing of a mixture of copper and zinc amine or precipitating/co-precipitating copper and zinc salt solution or other known processes for forming the copper oxide/zinc oxide precursor material. The promoted catalyst with alkaline earth metal and/or transition metal promoters is prepared by adding these promoters to the copper oxide/zinc oxide precursor material. It is preferred that the promoters are added onto the particle surface of copper/zinc species by impregnation after formation of the copper/zinc species and are not precipitated onto particles with zinc species alone.

The invention is also a process for the conversion of aldehydes to corresponding alcohols using a copper oxide/zinc oxide catalyst containing as promoters one or more alkaline earth metal compounds and/or one or more transition metal compounds without precipitation occurring from the transition metal promoters.

DETAILED DESCRIPTION OF THE INVENTION

Disclosed as embodiments of the present invention are catalysts useful for hydrogenating aldehydes to alcohols, catalytic processes for hydrogenating aldehydes to corresponding alcohols, and processes for the production of these catalysts, wherein the catalysts reduce the quantity of undesirable by-products produced by prior art catalysts during the catalytic process, yet retain high selectivity and activity. These embodiments include catalysts for hydrogenating aldehydes to corresponding alcohols comprising copper oxide, zinc oxide, and selectivity enhancers comprising at least one or more alkaline earth metal or one or more transition metal or combinations thereof.

The precursor material for the catalyst for hydrogenating aldehydes to the corresponding alcohols, prior to addition of the selectivity enhancers or support, comprises a copper oxide/zinc oxide material, wherein from about 10 to about 70% by weight of the material comprises copper oxide. The zinc oxide component comprises from about to about 90% by weight. In other embodiments, the material comprises about 20 to 50% by weight of copper oxide and about 50 to 80% by weight of zinc oxide.

Aldehyde hydrogenation precursor catalyst compositions containing a mixture of copper oxide and zinc oxide useful in the present invention may be prepared by any one of a variety of known methods suitable for manufacturing such precursor catalytic materials. Thus, an intimate mixture of copper oxide and zinc oxide may be prepared by blending the metal oxides together, for example, by titration processes or by fusing a mixture of the oxides and then grinding the fused, solidified mass. In one alternative embodiment, the mixture is prepared by precipitating/co-precipitating a mixture of copper and zinc compounds from an aqueous solution of copper and zinc salts, which can then be converted (decomposed) to their oxides.

Alternatively, the mixture of copper oxide and zinc oxide can be prepared by the simultaneous decomposition of ammine complexes, as for example, soluble copper and zinc tetra-ammine carbonates or soluble copper and zinc di- or tri-ammine carbonates. An aqueous mixture of copper and zinc ammine complexes in the desired copper to zinc weight ratio is heated for a sufficient period of time to liberate ammonia and unreacted carbon dioxide and to precipitate the water-insoluble basic carbonates. The resulting slurry can then be filtered or spray dried followed by calcination.

As previously advised, hydrogenation catalysts of the prior art have exhibited one or more disadvantages when used for commercially hydrogenating aldehydes to alcohols. One of the significant problems associated with these prior art catalyst is the production of significant amounts of by-products, particularly esters. These esters can be formed from two side reactions. The first is the reaction of aldehydes within the aldehyde feed. The second reaction is the reaction between the aldehydes in the feed and the alcohol product which is produced by the reaction. The reaction rate of the aldehyde/alcohol reaction is higher than that of the aldehyde/aldehyde reaction. While not wishing to be bound by any theory, applicants believe that alkaline earth metal compounds, when used as promoters of the copper oxide/zinc oxide catalyst, reduce the production of esters formed in this aldehyde/alcohol reaction.

Accordingly, in one embodiment, the promoter comprises an alkaline earth metal compound or a mixture of alkaline earth metal compounds used alone. When converted to its oxide form during the process for the production of the catalysts, when one or more alkaline earth metal compounds alone comprise the promoters, the alkaline earth metal promoter(s) comprises from about 0.1 to about 9% by weight of the catalyst. Alternatively, the alkaline earth metal promoter(s) comprises from about 0.8 to about 4% by weight of the catalyst.

While alkaline earth metal compounds are believed to reduce the aldehyde/alcohol reaction, applicants further believe that transition metal promoters suppress the aldehyde/aldehyde reaction for the production of esters. Accordingly, in another embodiment, when suppression of this aldehyde/aldehyde reaction is important, the promoter comprises a transition metal compound or a mixture of transition metal compounds used alone. When converted to its oxide form during the process for the production of the catalyst, when one or more transition metal compounds alone comprise the promoters, the transition metal promoter comprises from about 0.1 to about 7% by weight of the catalyst. Alternatively, the transition metal oxide promoter comprises from 0.5 to 4% by weight of the catalyst.

It has been discovered that, generally, suppression of the aldehyde/alcohol reaction is more important than the suppression of the aldehyde/aldehyde reaction for the production of esters. Notwithstanding, alcohol manufacturers may wish to utilize various combinations of alkaline earth metal promoters and transition metal promoters depending upon the composition of the aldehyde feed that is used for the reaction or the structure and layers of the catalyst system. Notwithstanding, it has been discovered that generally alkaline earth metal promoters work better for the suppression of the ester reaction in conventional reactors, while the function of the transition metal promoters is limited. Notwithstanding, suppression of both reactions is often desired. Accordingly, in another embodiment, the promoters comprise one or more alkaline earth metal compounds used in combination with one or more transition metal compounds. When converted to their oxide form during the process for the production of the catalysts, this combination of promoters comprise an alkaline earth metal compound or compounds comprising from about 0.1 to about 7% and a transition metal compound or compounds comprising from about 0.2 to 5% by weight of the catalyst. Alternatively, the combination of promoters comprises an alkaline earth metal promoter or promoters comprising from about 0.1 to about 3% and a transition metal promoter or promoters comprising from about 0.6 to 2% by weight of the catalyst.

Depending upon the feed that is used as the structure and layers of the catalyst system, the promoter or promoters that are added to the copper oxide/zinc oxide catalyst can be modified and adjusted. Notwithstanding, generally alkaline earth metal promoters work better for the reduction of the side, ester reactions and the function of the transition metal promoters is limited. In fact, at high conversion rates, the alkaline earth metal promoters used without transition metal promoters work better than a combination of the alkaline earth metal and transition metal promoters. Notwithstanding, an industry reactor can be looked at as a two-bed system, wherein the top bed contacts a high aldehyde low alcohol content feed stream, while the lower bed contacts a feed stream with higher alcohol content. Thus, one preferred loading is the use of a copper oxide/zinc oxide catalyst to which has been added a transition metal promoter alone to suppress the aldehyde/aldehyde reaction in an upper bed with the lower bed containing a copper oxide/zinc oxide promoter with an alkaline earth metal promoter added alone to suppress the aldehyde/alcohol reaction. However, from a commercial standpoint, it is often preferred to use a single catalyst for the two beds of a reactor. Because of the importance of suppressing the aldehyde/alcohol reaction by-products, and to a lesser extent the aldehyde/aldehyde reaction products, added to the copper oxide/zinc oxide catalyst is both an alkaline earth metal promoter and a transition metal promoter, although a copper oxide/zinc oxide catalyst promoted with only an alkaline earth metal promoter also works well.

The alkaline earth metal and transition metal promoters may be added to the catalyst using water soluble compounds including inorganic salts, such as nitrates, sulfates and halides, and organic compounds, such as formates, acetates, oxalates, and other well known water soluble organic compounds. If the promoters are added as inorganic salts, the preferred embodiment is to add the additives directly to the calcined copper oxide/zinc oxide precursor material. If the promoter is an organic compound, the preferred embodiment is to add the promoter to the copper and zinc precipitate in the form of green cake. However, it is not an alternative embodiment to add the alkaline earth metal or transition metal promoters prior to the preparation of the copper/zinc precursor material. When this process is used, performance of the catalyst shows reduced activity and increased produced of undesired by products.

Suitable alkaline earth metals include, but are not limited to, magnesium, calcium and barium, alternatively magnesium and calcium. Suitable transition metals include, but are not limited to nickel, silver and cobalt.

In preparing the catalysts of the invention, any recognized method can be used to make the CuO/ZnO precursor as previously discussed. In one embodiment, copper and zinc solutions, such as chlorides, sulfates and nitrates, are blended and combined with a precipitation agent, such as sodium carbonate. The precipitated material is washed and substantially filtered to form a filter cake. The wet cake is followed by drying and calcination to convert the copper and zinc species to their oxide forms. Promoters comprising one or more alkaline earth metals and/or one or more transition metals, or combination thereof, as discussed above, are then added to the wet cake, dried, and/or calcined. In another embodiment, the promoter or promoters are added to the wet cake. The wet cake can be wetted with an aqueous solution of the one or more promoter compounds, dried, and then calcined to convert the promoters to their oxide form. Depending on the particular promoter or promoters used, and its addition step, calcination of the treated catalyst precursor also may be utilized.

Notwithstanding, other process have been disclosed for production of catalysts for aldehyde hydrogenation, such as disclosed in CN 1695802, wherein selectivity enhancers are combined with the zinc salt to produce a precursor material prior to combination with the copper salt. Catalysts produced by this process are not as effective, showing reduced selectivity and activity. Thus, this process is not recommended for production of an embodiment of the catalyst. It has been surprisingly discovered that catalysts produced by this process are not only less effect, they are structurally distinct from catalysts produced by the previously disclosed processes.

While the present catalyst can be used in an unsupported form, it may also include an inert support or binder, such as alumina, titania, silica, alumina-silica, cement, clay and other well recognized support and binder materials in quantities up to about 50 wt. %, by weight of the total weight of the catalyst.

The catalytic material can be used for hydrogenating a wide variety of straight or branched chain, saturated or unsaturated aldehydes containing from 2 to 22 carbon atoms. The aldehyde reactants also may contain other oxygenated groups. The feed stock is limited primarily, only by the practicability of vaporizing higher boiling aldehydes. Suitable aldehydes include, but are not limited to, saturated aldehydes like acetaldehyde, propionaldehyde, iso-butyraldehyde, n-butyraldehyde, isopentyl aldehyde, 2-methylpentaldehyde, 2-ethylhexyldehyde, 2-ethylbutyraldehyde, n-valeraldehyde, iso-valeraldehyde, carproaldehyde, methyl-n-propylacetaldehyde, iso-hexaldehyde, caprylaldehyde, n-nonylaldehyde, n-decanal, dodecanal, tridecanal, myristic aldehyde, pentadecaldehyde, palmitic aldehyde, stearic aldehyde and such unsaturated aldehydes as acrolein, methacrolein, ethacrolein, 2-ethyl-3-propylacrolein, crotonaldehyde and the like. The aldehyde may be in a substantially pure state or mixed with a component or components other than the aldehyde itself. Further, a mixture of aldehydes may be employed.

The aldehyde or mixture of aldehydes employed may be obtained by an oxo process. Either a portion or all of the product mixture or an oxo process, i.e., the reaction of olefins with carbon monoxide and hydrogen in the presence of a catalyst to add a carbonyl group at one of the carbon atoms of the olefinic group, can be used. Of course, the aldehyde or mixture of aldehydes can be obtained by processes other than the oxo process, such as by oxidation of olefins or saturated hydrocarbons or by an aldol condensation. The present invention is not limited to the source of any particular aldehyde.

The aldehyde in a vaporous state is contacted with the hydrogenation catalyst in the presence of a hydrogen-containing gas. While substantially pure hydrogen alone can be used, hydrogen in admixture with other gases that are desirably inert, may be added to the aldehyde and catalyst. Suitable inert gases for mixing with hydrogen are nitrogen and methane. The term "hydrogen-containing gas" includes both substantially pure hydrogen gas as well as gaseous mixtures containing hydrogen.

Normally, the hydrogenation reaction is conducted at a temperature of at least about 100° C. and, because of the high selectivity of the present catalyst, can be conducted at a temperature as high as about 300° C. The reaction may be carried out at a temperature in the range of about 120° C. to 260° C. This temperature range balances the competing factors of energy and reaction rate. The reaction can be conducted at any suitable pressure from atmospheric up to about 600 psig. In view of the need to maintain the aldehyde and alcohol products in the vaporous state above the dew point, reaction pressure is somewhat influenced by reaction temperature, the aldehyde undergoing hydrogenation and the quantity of hydrogen-containing gas. Space velocities for the hydrogenation reaction may range from about 0.1 to about 8.0 based on the liquid volume of aldehyde fed to the vaporizer per volume of catalyst per hour.

The process of the present invention may be carried out in a continuous manner. In this embodiment, the aldehyde, the mixture of aldehydes, or the oxo reaction products are vaporized as needed and brought together with the hydrogen-containing gas at the desired temperature and pressure over the catalyst of the present invention. Alternatively, the catalyst may be used in a fixed catalyst bed reactor. The reaction zone may be an elongated tubular reactor with the catalyst supported within the tubes. Adiabatic tank type reactors also can be used. In such reactors, the heat of reaction causes an increase in reaction temperature from reactor inlet to reactor outlet.

The promoted catalysts promoted with one or more alkaline-earth metals and/or one or more transition metals, are able to suppress ester formation at high temperatures and high alcohol concentrations. Thus, adiabatic reactors can be used to their fullest potential. The catalysts also may be used in an isothermal or near isothermal reactor, wherein the catalyst is contained in cooled tubes or cooling tubes are placed within a fixed bed catalyst. As noted above, good selectivity can be obtained using the catalysts of the embodiments of the present invention even when the entire catalyst bed is operated near its maximum temperature. Under such conditions, the heat of reaction can be recovered as useful energy, such as, for example, by generating high pressure steam.

Alcohol products recovered from the hydrogenation reaction are separated from unreacted hydrogen by condensation and excess hydrogen is recompressed and recycled to the reaction zone. The crude alcohol product can be used as is, or it can be further purified using conventional techniques such as fractional distillation. Unreacted aldehyde, which also may be recovered, can be recycled.

The following examples are presented to illustrate the embodiments of the present invention and are not intended to constitute a limitation on their scope, which is defined in the appended claims.

Example 1

Comparative

Copper oxide-zinc oxide catalyst (without promoters) (R-1) is prepared by a process consistent with Example 5A of U.S. Pat. No. 4,876,402.

16 liters of copper and zinc nitrate solution (containing 417 g copper and 858 g zinc) was heated to about 110° F. (43° C.) and sprayed into 12.8 liter sodium carbonate solution (15.7%), which was mechanically agitated and maintained at about 140° F. (60° C.). The final pH of the precipitation mixture was about 7.0 to 8.5. The precipitated slurry was filtrated. The sodium in the wet cake was removed by washing and decanting with water. The sodium content was lowered to less than 0.1% in calcined filter cake. The wet cake was spray dried or/and calcined as designed by experiments. The final product was tab shaped with 2% graphite and contained about 32.1 wt. % CuO and about 65.9 wt. % ZnO.

Example 2

Comparative

A reference catalyst with promoters of Ni and K was prepared using Ni nitrate and K nitrate precursors (R-2) was prepared based on Example 5E of U.S. Pat. No. 4,876,402.

An aqueous slurry of the catalyst precursor, graphite, Ni nitrate and K nitrate in sufficient amounts to provide a calcined catalyst composition of 0.7% $K_2O$, 3.0% NiO, 2.0% graphite, 30.9% CuO and 63.4% ZnO was made. The dried powder was tableted and calcined at 370° C. to decompose the nitrates.

Example 3

Comparative

A reference catalyst with promoters Mg and Al was prepared by a process consistent with Example 2 of CN 1695802. (R-3)

450 ml of a copper nitrate solution (40.7 g CuO) was made by dissolving copper nitrate salt. 700 ml of a zinc nitrate solution (100.7 g ZnO) is made by dissolving zinc nitrate salt. 150 ml of the above zinc nitrate solution was mixed with a solution of 5.8 g magnesium nitrate and 41 g aluminum nitrate. The mixed solution was coprecipitated using a 15.7% sodium carbonate solution at 75 to 85° C. at a pH between 7.9 and 8.5. After aging for 30 minutes at 60° C. the material was filtered to obtain a filter cake. The remaining zinc nitrate solution was mixed with the copper nitrate solution followed by coprecipitation with a 15.7% sodium carbonate solution at 75 to 85° C. at a pH between 7.9 and 8.5. After aging for 30 minutes the solution was filtered to produce filter cake II. The two filter cakes were mixed and washed four times and 45 to 60° C. The final filter cake was dried and calcined at 350° C. for nine hours to produce the catalyst.

Example 4

Inventive

A catalyst was made with promoter Ag nitrate (I-1).

1.7 g silver nitrate was dissolved in 15 ml of water. 50 g of the catalyst of Example 1 were wetted with 15 ml of water. The silver nitrate solution was added to the wetted Example 1 catalyst, which was slurried with stirring. The slurry mixture was dried and calcined. The final product was tabbed with 2.0% graphite resulting in a catalyst composition of 2.3 $Ag_2O$, 2.0% graphite, 31.9% CuO and 63.8% ZnO.

Example 5

Inventive

A catalyst was made with promoter Mg nitrate (I-2).

1.9 g magnesium nitrate hexahydrate was dissolved in 15 ml of water. 50 g of the catalyst of Example 1 were wetted with 15 ml of water. The magnesium nitrate solution was added to wetted Example 1 catalyst, which was slurried with stirring. The slurry mixture was dried and calcined. The final product was tabbed with 2.0% graphite resulting in a catalyst composition of 0.6% MgO, 2.0% graphite, 32.4% CuO and 65% ZnO.

Example 6

Inventive

A catalyst (I-3) was made the same as Example 5 except the quantity of magnesium nitrate hexahydrate was increased to 9.5 g resulting in a catalyst comprising 3.0% MgO, 2.0% graphite, 31.6% CuO and 63.4% ZnO.

Example 7

Inventive

A catalyst (I-4) was made the same as Example 5 except the magnesium nitrate hexahydrate was replaced with 8 g magnesium acetate tetrahydrate resulting in a catalyst comprising 3.0% MgO, 2.0% graphite, 31.6% CuO and 63.4% ZnO.

Example 8

Inventive

A catalyst (I-5) was made the same as Example 4 except the silver nitrate was replaced with 1.3 g calcium nitrate tetrahydrate resulting in a catalyst comprising 0.6% CaO, 2.0% graphite, 32.4% CuO and 65.0% ZnO.

Example 9

Inventive

A catalyst (I-6) was made using as promoters magnesium and silver. 9.5 g magnesium nitrate hexahydrated was dissolved in 15 ml water. 1.7 g silver nitrate was dissolved in 15 ml water. 50 g of the catalyst of Example 1 were wetted with 15 ml of water. The magnesium nitrate solution was added to the wetted Example 1 catalyst. Then the silver nitrate solution was added to the mixture to form a slurry. The slurried solution was stirred, dried and calcined. The final product was tabbed with 2.0% graphite, resulting in a catalyst composition of 2.3% $Ag_2O$, 3.0% MgO, 30.9% CuO and 61.8% ZnO and 2.0% graphite.

Example 10

Inventive

A catalyst (I-7) was prepared by the process of Example with the promoters comprising nickel and barium. The magnesium nitrate was replaced with 0.34 g of barium hydroxide and the silver nitrate was replaced with 2.9 g nickel nitrate resulting in a catalyst composition of 1.5% NiO, 0.6% BaO; 31.9% CuO, 64.0% ZnO and 2.0% graphite.

Example 11

Inventive

A catalyst (I-8) was prepared by the process of Example 10, except the promoters were nickel and magnesium. The quantity of nickel was 2.9 g nickel nitrate and the quantity of magnesium was 1.9 g magnesium nitrate resulting in a catalyst composition of 1.5% NiO, 0.6% MgO, 31.9% CuO, 64.0% ZnO and 2.0% graphite.

Kinetic tests were performed on the catalysts of the Examples in a set of R&D lab tubular reactors (¼" tube) with vapor phase hydrogenation of butyraldehyde to butanol under the following conditions: 210° C., 50 psi, 15:1 hydrogen: aldehyde ratio, and 8/h LHSV. The catalysts were reduced using a 5% $H_2$ in a $H_2$ gas stream before reaction.

The results of the tests are listed in the following Table 1.

TABLE 1

| Catalyst | R-1 | R-2 | R-3 | I-1 | I-2 | I-3 | I-4 | I-5 | I-6 | I-7 | I-8 |
|---|---|---|---|---|---|---|---|---|---|---|---|
| Butyraldehyde conversion, % | 82.7 | 81.2 | 81.1 | 78.9 | 83.9 | 83.9 | 82.5 | 82.2 | 83.7 | 86.0 | 84.4 |
| Butyl Butyrate, % | 0.38 | 0.09 | 0.41 | 0.30 | 0.25 | 0.11 | 0.19 | 0.16 | 0.14 | 0.15 | 0.14 |

The catalysts promoted with an alkaline earth metal and/or a transition metal, retained their bulk structure and surface features. As is clear from the Examples, the catalysts promoted with an alkaline earth metal or a transition metal alone or in combination significantly suppressed the major byproduct formation. Comparing the samples prepared with the technology disclosed in the prior art, the samples produced by the process disclosed by the Examples, using alkaline earth metal compounds, and/or transition metal compounds as precursor materials, showed higher activity with better selectivity. Note particularly the improvement in performance of Inventive Example 9, 10 and 11 (I-6, I-7 and I-8), where a combination of an alkaline earth metal and a transition metal promoter was used, in comparison with reference Example 3 prepared by the process of CN 1645802 (R-3).

The principals, preferred embodiments and modes of operation of the embodiments of the present invention have been described in the foregoing specification. The embodiments which are intended to be protected herein are not to be considered or limited to the particular terms of disclosures as these are regard as being illustrative rather than restrictive. Variations and changes may be made by those skilled in the art without departing from the embodiments of the invention.

The invention claimed is:

1. A catalyst for hydrogenating aldehydes to alcohols comprising from about 10 to about 70 wt. % copper oxide, from about 30 to about 90 wt. % zinc oxide and one or more alkaline earth metal promoters and one or more transition metal promoters.

2. The catalyst of claim 1 wherein the alkaline earth metal is selected from the group consisting of magnesium, calcium, barium and mixtures thereof.

3. The catalyst of claim 1 wherein the transition metal is selected from the group consisting of nickel, cobalt, silver, and mixtures thereof.

4. The catalyst of claim 1 wherein the promoters consist essentially of one or more alkaline earth metal promoters and one or more transition metal promoters.

5. The catalyst of claim 1 wherein the alkaline earth metal promoter comprises from about 0.1 to about 9.0 wt % of the catalyst after conversion to an oxide form.

6. The catalyst of claim 1 wherein the alkaline earth metal promoter comprises from about 0.8 to about 4.0 wt % of the catalyst after conversion to an oxide form.

7. The catalyst of claim 1 wherein the transition metal promoter comprises from about 0.1 to about 7 wt. % of the catalyst after conversion to an oxide form.

8. The catalyst of claim 7 wherein the transition metal oxide promoter comprises from about 0.5 to about 4 wt. % of the catalyst.

9. The catalyst of claim 1 wherein the promoters are combined with the copper oxide and zinc oxide only after precursors of the copper oxide and precursors of zinc oxide have been combined to form a precursor material.

10. A process for preparation of a catalyst for hydrogenating aldehydes to alcohols comprising:

preparing a blend of a zinc compound and a copper compound to form a zinc/copper precursor material after formation of the blend of the copper compound and the zinc compound;

mixing promoters comprising one or more alkaline earth metal compounds and one or more transition metal compounds, with the zinc/copper precursor material, calcining the mixture; and forming the catalyst.

11. The process of claim 10 wherein the promoters consist essentially of one or more alkaline earth metal promoters and one or more transition metal promoters.

12. The process of claim 10 wherein the promoters are not combined with a zinc salt to produce a precursor material during production of the catalyst.

13. The process of claim 11 wherein the promoters are not combined with a zinc salt to produce a precursor material during production of the catalyst.

14. A catalyst for hydrogenating aldehydes to alcohols comprising about 20 to 50% by weight of copper oxide, about 50 to 80% by weight of zinc oxide, about 0.8 to about 4% by weight of a magnesium compound and from about 0.1 to about 3% by weight of a nickel compound or a silver compound.

15. A process of hydrogenating aldehydes to alcohols comprising contacting an aldehyde in the presence of a hydrogen-containing gas with the catalyst of claim 1 at a temperature of at least about 100° C. and a pressure from atmospheric up to about 600 psig.

* * * * *